United States Patent [19]

Yamaguchi et al.

[11] Patent Number: 5,275,756
[45] Date of Patent: Jan. 4, 1994

[54] FLUORINE-CONTAINING OPTICALLY ACTIVE COMPOUND AND LIQUID CRYSTAL COMPOSITION CONTAINING THE SAME

[75] Inventors: Akio Yamaguchi; Shigeru Mitsuhashi, both of Tokyo; Mamoru Yamada; Minzo Sakaguchi, both of Kanagawa; Hiroshi Sugiyama, Tokyo; Hiroko Konuma, Tokyo; Hitoshi Kondo, Tokyo; Toshimitsu Hagiwara, Tokyo, all of Japan

[73] Assignee: Takasago International Corporation, Tokyo, Japan

[21] Appl. No.: 738,638

[22] Filed: Jul. 31, 1991

[30] Foreign Application Priority Data

Jul. 31, 1990 [JP] Japan .................... 2-201164

[51] Int. Cl.$^5$ ............... C09K 19/34; C09K 19/52; C07D 239/02
[52] U.S. Cl. .............. 252/299.61; 252/299.01; 544/298; 544/335
[58] Field of Search ............ 252/299.01, 299.61; 544/298, 335

[56] References Cited

U.S. PATENT DOCUMENTS 5,120,468  6/1992  Saito et al. .............. 252/299.61

FOREIGN PATENT DOCUMENTS 0278665  8/1988  European Pat. Off. .
0293910  12/1988  European Pat. Off. .
9013611  11/1990  PCT Int'l Appl. .

Primary Examiner—Robert L. Stoll
Assistant Examiner—Shean C. Wu
Attorney, Agent, or Firm—Sughrue, Mion, Zinn, Macpeak & Seas

[57] ABSTRACT

A fluorine-containing optically active compound represented by formula (I):

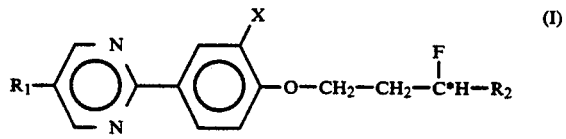

wherein $R_1$ represents a straight chain alkyl or alkoxy group having from 6 to 14 carbon atoms or a 4-alkylphenyl or 4-alkoxyphenyl group having from 8 to 12 carbon atoms; $R_2$ represents a straight chain alkyl group having from 1 to 8 carbon atoms; $C^*$ represents an asymmetric carbon atoms; and X represents a hydrogen atom or a fluorine atom, provided that X represents a fluorine atom when $R_1$ contains a phenyl group, and a liquid crystal composition containing the same are disclosed. The compound (I) has large spontaneous polarization and low viscosity to achieve a fast response time. In the N* phase of the compound (I), the helical pitch has small temperature dependence.

2 Claims, 3 Drawing Sheets

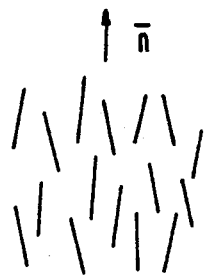
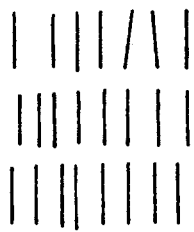
NEMATIC PHASE
SMECTIC A PHASE
SMECTIC C PHASE
FIG. 2
+ CHIRAL DOPANT
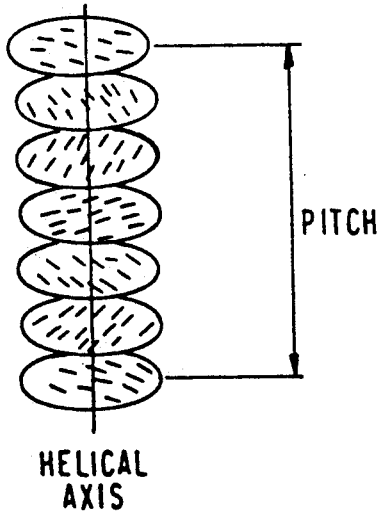
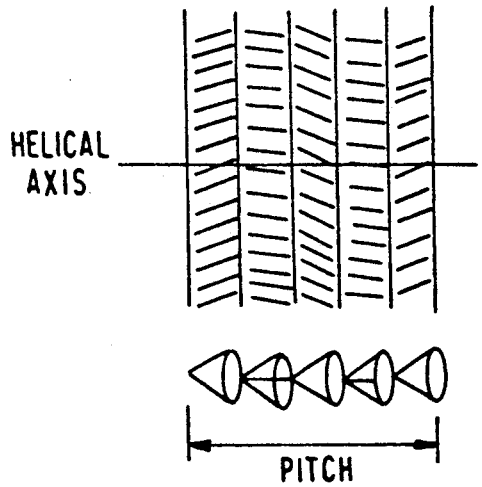
PITCH
HELICAL AXIS
HELICAL AXIS
PITCH
FIG. 1
FIG. 3

FLUORINE-CONTAINING OPTICALLY ACTIVE COMPOUND AND LIQUID CRYSTAL COMPOSITION CONTAINING THE SAME

FIELD OF THE INVENTION

This invention relates to a novel optically active compound and a liquid crystal composition containing the same which be used in liquid crystal electrooptical elements, particularly in devices utilizing electrooptical effects, such as liquid crystal displays and optical switching elements.

BACKGROUND OF THE INVENTION

Liquid crystal displays have been used in various embodiments such as watches and desk calculators because of their flatness, lightness, and low electric power consumption. With the advancement of integrated circuits (IC), liquid crystal displays have been increasing the display size and extending their use in computers, liquid crystal TV sets, etc. in place of conventional cathode-ray tubes. However, nematic liquid crystals which have conventionally been used have a slow response time of from 10 to 50 milliseconds and undergo a reduction in display contrast according as the number of pixels increases.

In the state-of-the-art liquid crystal displays, the above-described disadvantage is coped with by fitting each pixel with a thin film transistor (TFT) to achieve so-called active matrix driving or by increasing the angle of twist of liquid crystal molecules sandwiched between a pair of substrates to 220° to 270° (super-twisted nematic: STN).

Mounting of TFT according to the former means not only entails very high cost but has a poor yield, resulting in an increased production cost. Cost reduction by introducing a large-scale production line having been studied, there is a limit due to essential involvement of many production steps. Further, ever since the appearance of high-definition televisions (HDTV), there has been an increasing demand of liquid crystal displays making a high-content display. In nature of TFT and nematic liquid crystals, it is nevertheless considered very difficult to increase display density.

On the other hand, although the STN mode exhibits an increased contrast ratio, it has a slower response time of from 100 to 200 milliseconds and is thus limited in application.

It has therefore been keenly demanded to develop a liquid crystal element which achieves high-density displaying at a high rate of response. Ferroelectric liquid crystal display elements form the nucleus of such expectations. Ever since the report of N. A. Clark, et al. on surface-stabilized ferroelectric liquid crystal devices (SSFLD) (refer to N. A. Clark, et al., *Appl. Phys. Lett.*, Vol. 36, p. 899 (1980), extensive studies have been directed to ferroelectric liquid crystals with the attention on their fast response time. However, ferroelectric liquid crystal display elements have not yet been put into practical use due to problems of response rate, molecular orientation, etc. still remaining unsolved. For example, the molecular orientation of ferroelectric liquid crystals proved more complicated than suggested by Clark, et al. That is, the director of liquid crystal molecules is apt to be twisted in smectic layers, under which a high contrast cannot be obtained. Further, the layers have been believed to be aligned upright and perpendicular to the upper and lower substrates (bookshelf structure) but, in fact, were found to have a bent structure (chevron structure). As a result, zigzag defects appear to reduce a contrast ratio. As an approach to solutions to these orientation problems, improved orientation methods have recently been proposed, such as use of an oblique SiO-deposited technique.

With respect to response time, it was believed in the early stage of studies that ferroelectric liquid crystal elements have a response in several microseconds. In fact, however, the highest of the so far reached response time is only several tens of microseconds. That is, in ferroelectric liquid crystal elements, since a response time of one pixel decides a refreshing time of a display unlike nematic liquid crystal elements, advantages of ferroelectric liquid crystals cannot be made full use of unless a fast response time of from 20 to 30 microseconds or less is reached. A response time is considered dependent on spontaneous polarization and rotational viscosity of liquid crystal materials and intensity of the applied electric field. Considering a limit of voltage which can be applied in practice with IC, a substantial improvement in response time must be realized through optimization of rotational viscosity and spontaneous polarization of liquid crystal materials. Under the present situation, sufficiently fast response time has not yet been obtained.

Hence, a search has been made preponderantly for compounds having large spontaneous polarization and liquid crystal compounds having low rotational viscosity. However, compounds exhibiting high spontaneous polarization generally have high viscosity, and few compounds satisfying both of these requirements have been discovered.

In general, a ferroelectric liquid crystal material comprises an achiral base liquid crystal composition showing a smectic C phase (Sc phase) to which an optically active compound called chiral dopants are added to form a ferroelectric liquid crystal composition. This is because, for one thing, performance requirements cannot be satisfied by a single material and, for another thing, it is aimed at to allot each of required performance properties to each compound so as to make a mixed system as simple as possible taking advantage of the fact that various physical properties including orientation vary depending on the structure of liquid crystal compounds used. Namely, in order to satisfy many physical properties required for ferroelectric liquid crystals, it is advantageous to divide the functions among components as simply as possible. In many cases, phenylpyrimidine type liquid crystal compounds having advantageous viscosity properties are utilized as an achiral base. In actual use, however, properties of the resulting ferroelectric composition, such as viscosity and response time, greatly vary depending on the properties of optically active compounds added thereto. Accordingly, an optically active compound to be added is required to exhibit moderate spontaneous polarization and low viscosity to provide a liquid crystal composition exhibiting a fast response time while giving no adverse influence on the performance of the achiral base, such as a temperature range.

Further, in order to obtain satisfactory orientation, ferroelectric liquid crystals are often required to have a smectic A phase in which orientation can be effected with relative ease and, if possible, a nematic phase in a higher temperature range. This being the case, when a chiral dopant is added to an achiral base having a phase sequence of isotropic, nematic, $S_A$ and Sc phase, the N and Sc phases become a chiral nematic phase (N* phase) and a chiral smectic phase (Sc* phase), respectively, in which a helical structure is induced as shown in FIGS. 1 and 3.

In order that the ferroelectric liquid crystals show satisfactory orientation and satisfactory bistability for use as a ferroelectric liquid crystal optoelectronic element, the N* phase and Sc* phase should have a helical pitch several times longer than the cell thickness. To achieve this, addition of only one kind of a chiral dopant is not sufficient, and it is necessary to use a chiral dopant in combination with an optically active compound showing an opposite helical sense. Besides, every optically active compound has its own direction, positive or negative, in spontaneous polarization. The helical sense of the N* and Sc* phases and the direction of spontaneous polarization are decided by the structure of the optically active compound without being correlated to each other. Therefore, mixing of optically active compounds makes the problem more complicated.

Hence, it is required to control the helix in the N* and Sc* phases with optically active compounds of as small kinds as possible while obtaining effective spontaneous polarization.

The problem to be considered here is temperature dependence of the helical pitch in the N* and Sc* phases induced by a chiral dopant. As mentioned above, the helical pitch is required not only to be sufficiently longer over the cell thickness but to have small temperature dependence. Even with a sufficiently long helical pitch, large temperature dependence results in great variation of orientation.

The importance of temperature dependence of a helical pitch also applies to a chiral dopant to be added to nematic liquid crystals which are used in twisted nematic (TN) and also STN mode display elements. For example, if a chiral dopant to be used shows high positive dependence on temperature (i.e., the pitch is broadened with an increase in temperature), it must be mixed with a chiral dopant having an opposite tendency to offset the temperature dependence, which makes the chiral dopant mixing system more complicated.

Thus, optically active compounds and compositions thereof for use in ferroelectric liquid crystal elements are demanded to satisfy a variety of performance properties. Accordingly, an optically active compound which has a fast response time, which does not have great influences on the temperature range of an achiral base, and whose helical pitch has small temperature dependence is very important for advancement of ferroelectric liquid crystals. For the time being, only a few of such compounds have been reported.

Further, chiral dopants currently used for nematic liquid crystals comprise a mixture of at least 4 kinds of optically active compounds for the purpose of the control of helical pitch in the N* phase and reducing the temperature dependence of the helical pitch. Not a few of these optically active compounds exhibit no liquid crystalline properties and, when added to a nematic liquid crystal, cause a drop of the nematic phase-isotropic phase transition temperature.

SUMMARY OF THE INVENTION

An object of the present invention is to provide an optically active compound useful as a ferroelectric liquid crystal, which has a large spontaneous polarization, a low viscosity, and a fast response time, the helical pitch in the N* phase, etc. of which shows small dependence on temperature.

Another object of the present invention is to provide an optically active compound useful as a chiral dopant for nematic liquid crystals to induce a chiral nematic phase whose helical pitch shows small temperature dependence.

The inventors have conducted extensive investigations to develop a compound which has a large spontaneous polarization and low viscosity for accomplishing a fast response time of a ferroelectric liquid crystal material and which exhibits an N* phase whose helical pitch has small temperature dependence, and reached the present invention.

The present invention relates to a fluorine-containing optically active compound represented by formula (I):

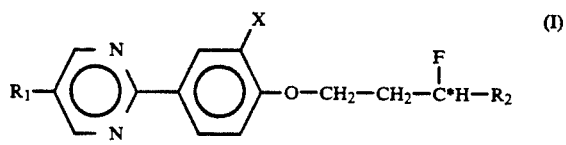

wherein $R_1$ represents a straight chain alkyl or alkoxy group having from 6 to 14 carbon atoms or a 4-alkylphenyl or 4-alkoxyphenyl group having from 8 to 12 carbon atoms; $R_2$ represents a straight chain alkyl group having from 1 to 8 carbon atoms; C* represents an asymmetric carbon atom; and X represents a hydrogen atom or a fluorine atom, provided that X represents a fluorine atom when $R_1$ contains a phenyl group.

The present invention also relates to a liquid crystal composition containing the compound of formula (I).

BRIEF DESCRIPTION OF THE DRAWINGS

FIGS. 1, 2, and 3 each illustrate the molecular orientation or structure of a nematic phase, a smectic A phase, and a smectic C phase, respectively.

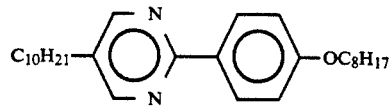

DETAILED DESCRIPTION OF THE INVENTION

Figure 4:
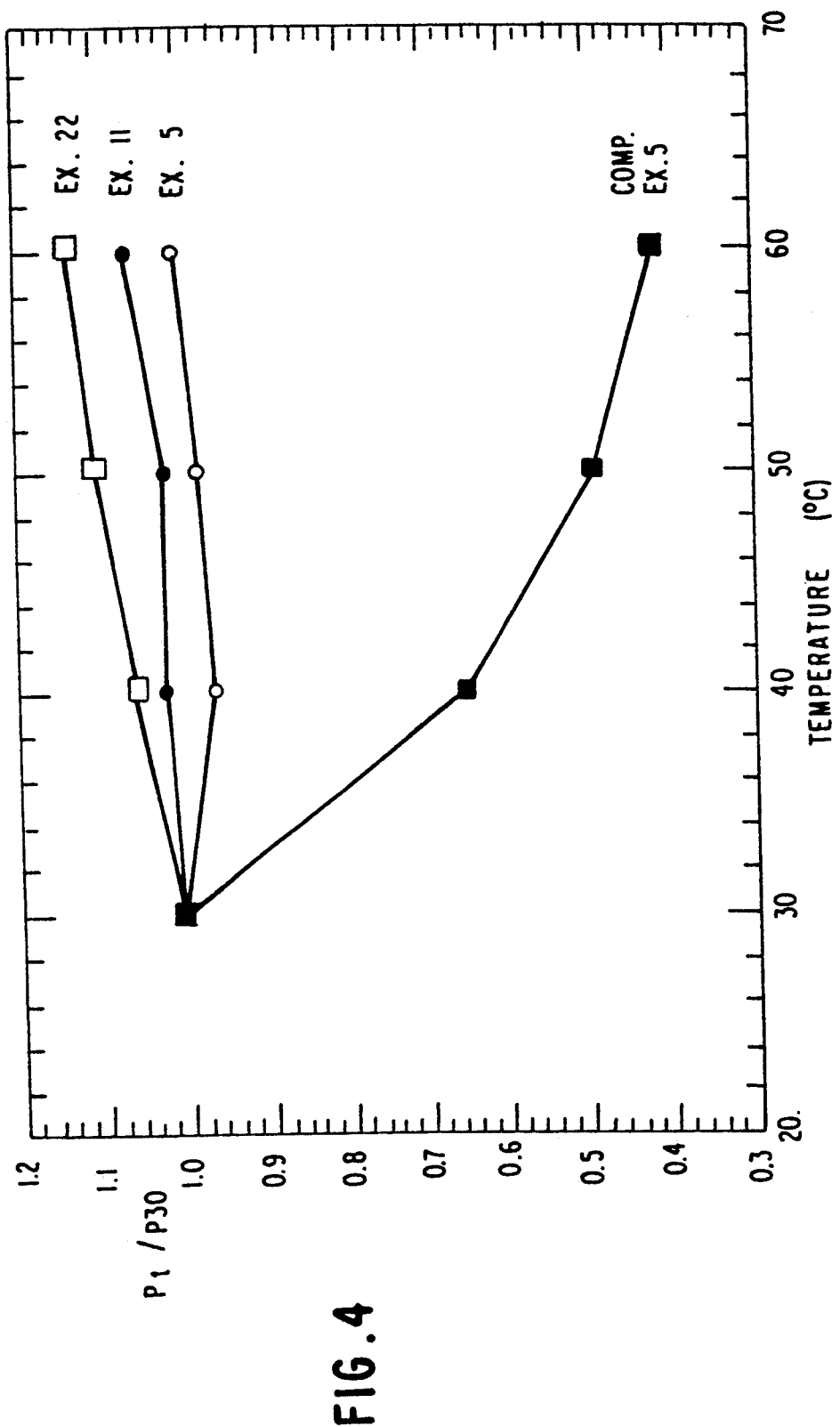
FIG. 4 is a graph showing temperature dependence of the helical pitch in the chiral nematic phase induced by incorporating 5% by weight of the compound according to the present invention or the comparative compound to a nematic liquid crystal composition (ZLI-2582).

Known compounds relevant to the optically active compounds of the present invention include ester type compounds having introduced therein a similar optically active group, reported by the present inventors (refer to JP-A-2-36154, the term "JP-A" as used herein means an "unexamined published Japanese patent application"). While these compounds responde at a higher rate as compared with conventional phenyl ester type optically active compounds, it has now been found that a further improved response time can be achieved by replacing the phenyl ester core with a phenylpyrimidine core.

The compounds used in Comparative Examples hereinafter described are also relevant to the compounds of the present invention (refer to JP-A-63-22042, Yahei, et al., *Dai* 13-*kai Erisho Toronkai Yokoshu*, 1Z02 (1987)). They are optically active compounds having a fluorine atom at the 2-position (2-fluoro compounds) and exhibit a fast response time and a relatively large spontaneous polarization. However, as described in JP-A-63-190842 suggesting similar compounds, the helical pitch in the N* phase of these 2-fluoro compounds shows considerable negative temperature dependence, which is an unfavorable property as a chiral dopant.

The compounds according to the present invention are optically active compounds having a fluorine atom at the 3-position.

Generally speaking, as an asymmetric carbon atom becomes farther from the core, the spontaneous polarization (Ps) is reduced by about one figure, and the response time is so reduced as illustrated below.

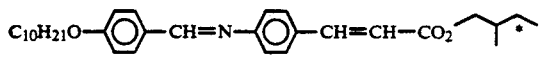

Ps: 3 nC/cm$^2$

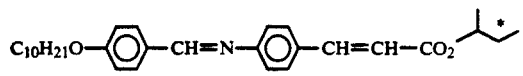

Ps: 17 nC/cm$^2$

In the compounds of the present invention, in spite that the asymmetric carbon atom is farther from the core than in the conventional compounds having a fluorine atom at the 2-position as shown in Comparative Examples hereinafter described (refer to JP-A-60-67453), the reduction in spontaneous polarization proved small. Besides, the compounds of the present invention have low viscosity and, eventually, exhibit substantially a similar response time. The helical pitch in the N* phase was also proved very small. Compounds having a fluorine atom at the 4-position (4-fluoro compounds) have a considerably reduced spontaneous polarization and a reduced response time as generally anticipated. Further, the compounds of the invention are entirely different, though similar in structure, from the comparative 2-fluoro or 4-fluoro compounds in phase sequence. In particular, the compounds of the invention are very easy to mix because they exhibit an N* phase necessary for obtaining satisfactory orientation.

On the other hand, compounds exhibiting a smectic phase of higher order are unfavorable because they make a lower side temperature range narrow when added to a liquid crystal composition. In this connection, a smectic phase of higher order often observed in the comparative 2-fluoro compounds does not appear in the compounds of the present invention. Therefore, the compounds of the present invention proved to have excellent properties required for a chiral dopant to be used in a ferroelectric liquid crystal composition.

In addition, it is generally received that heat stability of a liquid crystalline phase increases as its asymmetric carbon atom becomes farther from the core. The compounds of the present invention show increased heat stability in the Sc* phase as compared with the 2-fluoro compounds. However, it was also proved that the 4-fluoro compounds undergo reduction of heat stability in their Sc* phase.

The above-described difference in heat stability behavior in an Sc* phase exerts a great influences on mixing. That is, in order to assure an Sc* phase in a broad temperature range including room temperature, it is necessary to mix a plurality of achiral liquid crystal compounds differing in core structure. Cases are often met in which heat stability of the smectic C* phase is reduced by addition of an optically active compound. For example, when the 2-fluoro compound shown in Comparative Examples is added to an achiral base comprising a mixture of a phenylpyrimidine compound and an ester compound, the Sc* phase suffers from a considerable reduction in heat stability.

To the contrary, the compounds of the present invention can assure an Sc* phase in a broad temperature range including room temperature even when added to the same achiral base, thus making it feasible to provide a liquid crystal composition showing an Sc* phase in a broad temperature range including room temperature. The resulting liquid crystal composition has a low viscosity and a very fast response time.

Further, the optically active compounds according to the present invention show a chiral nematic phase whose helical pitch has small temperature dependence. Thus, where they are used as a chiral dopant for STN and TN mode liquid crystal elements, the phase transition temperature of the nematic phase received no great influence, and the helical pitch of the N* phase has small temperature dependence. Therefore, the compound of the present invention is mixed only for the purpose of adjustment of the pitch.

As described above, the optically active compounds of formula (I) can be used as a mixture with compounds having no optically active group and showing a mere smectic C phase. Specific examples of such compounds with which the compounds of the present invention can be mixed are shown below.

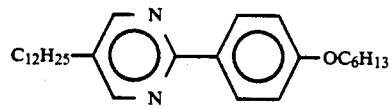

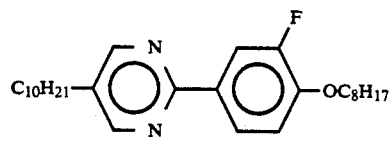

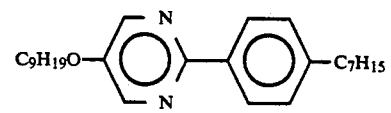

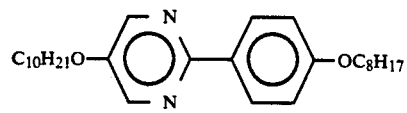

Liquid crystal compositions prepared by mainly using phenylpyrimidine compounds are particularly excellent in response time.

The compounds of the present invention exhibit very excellent properties as a chiral dopant to be added to nematic or smectic achiral base liquid crystals. The above-described findings are utterly unanticipated from reported facts. The present invention has been completed based on these findings.

In the optically active compounds represented by formula (I), in order to obtain a stable Sc* phase, $R^1$ is a straight chain alkyl or alkoxy group having from 6 to 14 carbon atoms or a 4-alkylphenyl group or 4-alkoxyphenyl group having from 8 to 12 carbon atoms, and $R^2$ is a straight chain alkyl group having from 1 to 8 carbon atoms. From the standpoint of viscosity, $R_2$ more preferably contains from 1 to 5 carbon atoms.

The optically active compounds of formula (I) can be synthesized as follows.

An optically active methyl 3-hydroxyalkanoate is fluorinated with hexafluoropropene diethylamine. This reaction is known to induce inversion. It was confirmed that the inversion proceeds nearly 100% without causing racemization. Thereafter, the fluorinated ester is reduced by using lithium aluminum hydride to obtain a 3-fluoroalkanol, which is then reacted with methanesulfonyl chloride to obtain 3-fluoroheptyl methanesulfonate. The resulting 3-fluoroheptyl methanesulfonate is reacted with a 5-alkyl- or 5-alkoxy-2-(4-hydro a 5-alkyl- or 5-alkoxy-2-(3-fluorophenyl-4-hydroxy)pyrimidine, or a 2-(3-fluoro-4-hydroxyphenyl)-5-(4-alkoxy- or 4-alkyl-phenyl)pyrimidine, which is synthesized by known processes described, e.g., in JP-A-61-22072, JP-A-61-200973, JP-A-63-16534, JP-A-63-153075, and JP-A-64-79160, to obtain the optically active compound of formula (I).

The present invention is now illustrated in greater detail with reference to Examples, but it should be understood that the present invention is not deemed to be limited thereto.

In the foregoing description and the following Examples, a cell used for measurements is a cell comprising a pair of glass substrates each having a transparent electrode on which a polyimide orientation membrane is coated and rubbed, assembled with a spacer therebetween at a gap of about 2.5 μm.

A spontaneous polarization (Ps) was obtained from a polarization inversion current with a triangular wave of ±10 V applied. A tilt angle was obtained from the extinction position under a crossed Nicol with a square wave of ±20 V applied. A response time was obtained from the speed of change of transmitted light under the same conditions as in the measurement of the angle of tile. The helical pitch in the chiral nematic phase was measured by use of a Cano's wedge cell.

Abbreviations used have the following meanings:
I: Isotropic liquid phase
N*: Chiral nematic phase
$S_A$: Smectic A phase
Sc*: Chiral smectic C phase
$S_3$: Unidentified smectic phase of higher order
Cr: Crystal phase
Tc: Sc*-$S_A$ Phase transition temperature
Ps: Spontaneous polarization

EXAMPLES 1 TO 7

Compounds shown in Table 1 below were synthesized. Synthesis of the compounds of Example 4 and 5 are described below.

Synthesis of
(S)-5-Decyl-2-[4-(3-fluoroheptyloxy)phenyl]pyrimidine
(Example 4)

1) Synthesis of Methyl (S)-3-Fluoroheptanoate:

In a 1 l flask were added 24.45 g of methyl (R)-3-hydroxyheptanoate (98.0% ee, $[\alpha]_D^{20} = -8.71°$), which was obtained by asymmetric hydrogenation of methyl 3-ketoheptanoate according to the process described in JP-A-63-310845, and 390 ml of methylene chloride in a nitrogen stream. The temperature of the mixture was kept at 5° to 10° C. A solution of 75 g of hexafluoropropene diethylamine (product of Tokyo Chemical Industry Co., Ltd.) in 225 ml of methylene chloride was added dropwise thereto at that temperature over 3 hours, followed by stirring for 2 hours. The reaction mixture was poured into 1200 ml of ice-water for liquid-liquid separation. The organic layer was washed with water, dried over magnesium sulfate, and freed of the solvent by distillation at 30° C. or lower. The residue was purified by silica gel column chromatography to obtain 12.4 g (yield: 48.5%) of the titled compound.

Incidentally, methyl (R)-3-fluoroheptanoate derived from methyl (S)-3-hydroxyheptanoate (98.8% ee, $[\alpha]_D^{20} = 9.07$) was hydrolyzed to obtain 3-fluoroheptanoic acid, which was then reacted with R-(+)-1-(1-naphthyl)ethylamine to form a diastereomer. The resulting diastereomer was found to have an optical purity of 98.7% ee by liquid chromatography, indicating that no racemization took place at all.

NMR (ppm): 0.92 (3H, t, J=7.2Hz), 1.36 (4H, m), 1.66 (2H, m), 2.62 (2H, m), 3.72 (3H, s), 4.93 (1H, m)

2) Synthesis of (S)-3-Fluoroheptanol:

To a 1 l flask were added 154 m of tetrahydrofuran and 2.3 g of lithium aluminum hydride in a nitrogen stream, and the solution was kept at 5° C. To the solution was added dropwise 9 g of methyl 3-fluoroheptanoate obtained in (1) above dissolved in 43 ml of THF over 2 hours at 5° C. After the addition, the temperature was gradually elevated up to room temperature, and the mixture was stirred for 2 hours. After cooling to 5° C., 2.3 g of water, 2.3 g of a 15% sodium hydride aqueous solution, and 6.9 g of water were added thereto dropwise in this order, followed by stirring at that temperature for 15 minutes. The thus formed precipitate was removed by filtration, and the filtrate was subjected to liquid-liquid separation. The organic layer was dehydrated over potassium carbonate and freed of the solvent by distillation at 30° C. or less to obtain 8.0 g (98.0%) of the titled compound.

NMR (ppm): 0.92 (3H, t, J=7.2Hz), 1.3–1.9 (8H, m), 3.81 (2H, m), 4.70 (1H, m)

3) Synthesis of (S)-3-Fluoroheptyl Methanesulfonate

To a 100 ml flask were added 8.7 g of (S)-3-fluoroheptanol and 21.5 g of pyridine in a nitrogen stream, and the solution was kept at 5° to 10° C. To the solution was added dropwise 7.5 g of methanesulfonyl chloride over 30 minutes, followed by stirring at 15° C. or less for 5 hours. The reaction mixture was poured into 200 ml of ice-water and extracted with ethyl acetate. The organic layer was washed successively with a diluted hydrochloric aqueous solution and water, dried over magnesium sulfate, and freed of the solvent by distillation at 30° C. or lower to obtain 12.7 g (93.18%) of the titled compound.

NMR (ppm): 0.92 (3H, t, J=7.1Hz), 1.35–1.8 (6H, m), 2.03 (2H, m), 3.02 (3H, s), 4.37 (2H, t, J=6.2Hz), 4.65 (1H, m)

4) Synthesis of (S)-5-Decyl-2-[4-(3-fluoroheptyloxy)-phenyl]pyrimidine:

In a 100 ml flask were added 3 g of 5-n-decyl-2-(4-hydroxy)phenylpyrimidine were added 1.9 g of potassium carbonate and 90 ml of dimethylformamide (DMF) in a nitrogen stream, and the mixture was stirred at room temperature. A solution of 2.2 g of 3-fluoroheptyl methanesulfonate in 12 ml of DMF was added dropwise thereto over 15 minutes. After the addition, the reaction mixture was gradually heated up to 80° C., followed by stirring at that temperature for 4 hours. After cooling, the reaction mixture was poured into a diluted hydrochloric acid aqueous solution and extracted with ethyl acetate. The extract was washed with water, dried over magnesium sulfate, and freed of the solvent by distillation to obtain 4.47 g of a residue. The residue was purified by silica gel column chromatography and recrystallized from ethanol to obtain 2.67 g (65.7%) of the titled compound.

$[\alpha]_D^{20} = +10.0°$

MS: 428 (M+)

NMR (ppm): 0.88 (3H, t, J=6.9Hz), 0.93 (3H, t, J=7.1Hz), 1.2–1.80 (24H, m), 2.09 (2H, m, J=7.5Hz), 4.18 (2H, m), 4.77 (1H, m), 6.99 (2H, d, J=9.0Hz), 8.36 (2H, d, J=9.0Hz), 8.58 (2H, s)

Synthesis of (R)-5-Dodecyl-2-[4-(3-fluoroheptyloxy)phenyl]pyrimidine (Example 5)

The titled compound was synthesized in a yield of 78.4% in the same manner as for the compound of Example 4, except for using 5-n-dodecyl-2-(4-hydroxyphenyl)pyrimidine and (R)-3-fluoroheptyl methanesulfonate.

$[\alpha]_D^{20} = -10.46°$
MS: 456 (M+)
NMR (ppm): 0.88 (3H, t, J=6.9Hz), 0.92 (3H, t, J=7.2Hz), 1.20–1.80 (26H, m), 2.08 (2H, m), 2.59 (2H, t, J=7.6Hz). 4.16 (2H, m), 4.78 (1H, m), 6.99 (2H, d, J=9.0Hz), 8.36 (2H, d, J=9.0Hz), 8.57 (2H, s)

The compound of Example 5 was mixed with a nematic liquid crystal composition "ZLI-2582" produced by Merck Co. at a mixing proportion of 5.0% by weight. The helical pitch of the N* phase thus induced was measured at a varying temperature and, as a result, proved to have very small temperature dependence as shown below.

| Measuring Temp. (°C.) | N* Phase Helical Pitch (μm) |
|---|---|
| 30 | 4.03 |
| 40 | 3.87 |
| 50 | 3.95 |
| 60 | 4.05 |

These results were plotted in FIG. 4, taking the helical pitch measured at 30° C. as a base. In FIG. 4, Pt means a pitch at t° C., and P30 means a helical pitch.

When the results are compared with those of Comparative Example 5 (hereinafter given) as shown in FIG. 4, it can be seen that the liquid crystal composition containing the comparative 2-fluoro compound has considerably large temperature dependence.

EXAMPLES 8 TO 12

Compounds shown in Table 1 were synthesized in the same manner as in Example 4. Synthesis of the compounds of Examples and 9 and the results of analyses are described below.

Synthesis of (R)-5-Heptyloxy-2-[4-(3-fluorooctyloxy)phenyl]pyrimidine (Example 8)

The titled compound was synthesized from 5-heptyloxy-2-(4-hydroxyphenyl)pyrimidine and (R)-3-fluorooctyl methanesulfonate.
Yield: 57.0%
$[\alpha]_D^{20} = -9.95°$
MS: 416 (M+)
NMR (ppm): 0.90 (6H, m), 1.30–1.80 (16H, m), 1.83 (2H, m), 2.08 (2H, m), 4.07 (2H, t, J=6.5Hz), 4.16 (2H, m), 4.80 (1H, m), 6.98 (2H, d, J=9.0Hz), 8.28 (2H, d, J=9.0Hz), 8.41 (2H, s)

Synthesis of (R)-5-Octyloxy-2-[4-(3-fluoroundecyloxy)phenyl]pyrimidine (Example 9)

The titled compound was synthesized from 5-octyloxy-2-(4-hydroxyphenyl)pyrimidine and 3-fluoroundecyloxy methanesulfonate.
Yield: 19.5%
$[\alpha]_D^{20} = +10.08°$
MS: 472 (M+)
NMR (ppm): 0.89 (6H, m), 1.25–1.80 (24H, m), 1.83 (2H, m), 2.08 (2H, m), 4.08 (2H, t, J=6.5Hz), 4.16 (2H, m), 4.77 (1H, m), 6.98 (2H, d, J=8.8Hz), 8.28 (2H, d, J=8.8Hz), 8.42 (2H, s)

(S)-5-Decyloxy-2-[4-(3-fluoroheptyloxy)phenyl]pyrimidine of Example 11 was mixed with ZLI-2582 at a mixing proportion of 5.07% by weight to determine temperature dependence of the helical pitch of the N* phase in he same manner as in Example 5. As a result, it was found that the pitch shows positive temperature dependence but its slope is very small as shown below and in FIG. 4.

| Measuring Temp. (°C.) | N* Phase Helical Pitch (μm) |
|---|---|
| 30 | 2.67 |
| 40 | 2.73 |
| 50 | 2.73 |
| 60 | 2.84 |

EXAMPLES 13 TO 23

Compounds shown in Table 1 were synthesized in the same manner as in Example 4. Synthesis of the compounds of Examples 15 and 16 and the results of analyses are shown below.

Synthesis of (R)-5-Nonyl-2-[8-fluoro-4-(3-fluoroheptyloxy)phenyl]pyrimidine (Example 15)

The titled compound was synthesized from 5-nonyl-2-(3-fluoro-4-hydroxyphenyl)pyrimidine and (R)-3-fluoroheptanol.
$[\alpha]_D^{20} = -10.98°$
MS: 432 (M+)
NMR (ppm): 0.88 (3H, t, J=6.9Hz), 0.93 (3H, t, J=7.2Hz), 1.20–1.80 (20H, m), 2.13 (2H, m), 2.60 (2H, t, J=7.7Hz), 4.24 (2H, m), 4.80 (1H, m), 7.05 (1H, t), 8.16 (2H, d), 8.58 (2H, s)

Synthesis of (R)-5-Decyl-2-[3-fluoro-4-(3-fluorohexyloxy)phenyl]pyrimidine (Example 16)

The titled compound was synthesized from 5-decyl-2-(3-fluoro-4-hydroxyphenyl)pyrimidine and (R)-3-fluorohexanol.
Yield 28.9%
$[\alpha]_D^{20} = -10.39°$
MS: 432 (M+)
NMR (ppm): 0.88 (3H, t, J=6.9Hz), 0.97 (3H, t, J=7.3Hz), 1.20–1.80 (20H, m), 2.12 (2H, m), 2.60 (2H, t, J=7.7Hz), 4.24 (2H, m), 4.82 (1H, m), 7/95 (1H, t), 8.16 (2H, d), 8.58 (2H, s)

(S)-5-Tetradecyl-2-[3-fluoro-4-(3-fluoroheptyloxy)phenyl]pyrimidine of Example 22 was mixed with ZLI-2582 at a mixing proportion of 5.01% by weight to determine temperature dependence of the helical pitch of the N* phase in the same manner as in Example 5. As a result, it was found that the pitch shows positive temperature dependence but its slope is very small as shown below and in FIG. 4.

| Measuring Temp. (°C.) | N* Phase Helical Pitch (μm) |
|---|---|
| 30 | 2.95 |
| 40 | 2.95 |
| 50 | 3.07 |

-continued

| Measuring Temp. (°C.) | N* Phase Helical Pitch (μm) |
|---|---|
| 60 | 3.07 |

EXAMPLES 24 TO 26

Compounds shown in Table 1 were synthesized in the same manner as in Example 4. Synthesis of the compound of Example 24 and the results of analysis are described below.

Synthesis of (R)-5-Hexyloxy-2-[4-(3-fluoroheptyloxy)phenyl]pyrimidine (Example 24)

The titled compound was synthesized from (R)-3-fluoroheptyl methanesulfonate, derived from methyl (S)-3-hydroxyheptanoate (98.0% ee, $[\alpha]_D^{20} = -8.71°$), and 5-n-hexyloxy-2-(4-hydroxy-3-fluorophenyl)pyrimidine.

Yield: 48.5%
$[\alpha]_D^{20} = -11.2°$
MS: 406 (M+)
NMR (ppm): 0.92 (6H, m), 1.30–1.90 (14H, m), 2.12 (2H, m), 4.08 (2H, t, J=6.5Hz), 4.23 (2H, m), 4.80 (1H, m), 7.04 (1H, t), 8.09 (2H, d), 8.41 (2H, s)

EXAMPLE 27

Synthesis of (R)-2-[3-Fluoro-4-(3-fluoroheptyloxy)phenyl]-5-(4-decylphenyl)pyrimidine In a 200 ml flask were charged 2.0 g of 2-(3-fluoro-4-hydroxyphenyl)-5-(4-decyloxyphenyl)pyrimidine synthesized by a known process, for example, the process disclosed in JP-A-63-253075 and JP-A-64-79160, 0.83 g of potassium carbonate, and 80 ml of DMF, followed by stirring at room temperature. A solution of 1.2 g of (R)-3-fluoroheptyl p-toluenesulfonate in 12 ml of DMF was added dropwise thereto over 15 minutes, followed by gradually heating up to 80° C. at which the mixture was allowed to react for 4 hours. After cooling, the reaction mixture was poured into a diluted hydrochloric acid aqueous solution and extracted with toluene. The extract was washed with water and freed of the solvent by distillation under reduced pressure to obtain 2.76 g of a crude product. The crude product was purified by silica gel column chromatography and recrystallized from a mixed solvent of ethanol and toluene to obtain 1.8 g of the titled compound.

$[\alpha]_D^{20} = -9.07°$
MS: 522 (M+)
NMR (ppm): 0.88 (3H, t, J=6.9Hz), 0.93 (3H, t, J=7.2Hz), 1.20–1.57 (18H, m), 1.60–1.80 (4H, m), 2.07–2.20 (2H, m), 2.67 (2H, t, J=7.7Hz). 4.26 (2H, m), 4.80 (1H, m), 7.08 (1H, t, J=8.4Hz), 7.33 (2H, d, J=8.3Hz), 7.52 (2H, m), 8.23 (2H, m), 8.95 (2H, s).

EXAMPLE 28

Synthesis of 2-[3-Fluoro-4-(3-fluoroheptyloxy)phenyl]-5-(4-dodecylphenyl)pyrimidine The titled compound was synthesized in the same manner as in Example 27.

EXAMPLE 29

Synthesis of 2-[3-Fluoro-4-(3-fluoroheptyloxy)phenyl]-5-(4-octyloxyphenyl)pyrimidine A mixture consisting of 1.18 g of 2-(3-fluoro-4-hydroxyphenyl)-5-(4-octyloxy)pyrimidine synthesized in the same manner as for the starting compound used in Example 27, 0.63 g of 3-fluoroheptyl methanesulfonate, 1.0 g of potassium carbonate, and 10 ml of DMF was allowed to react and worked up in the same manner as in Example 27. The resulting crude product was purified by silica gel column chromatography and recrystallized from ethanol to obtain 1.0 g of the titled compound.

$[\alpha]_D^{20} = -1.9°$
MS: 510 (M+)
NMR (ppm): 0.90–0.93 (6H, m), 1.25–1.85 (18H, m), 2.07–2.25 (2H, m), 4.02 (2H, t, J=6.5Hz), 4.26 (2H, m), 4.82 (1H, m), 7.05 (3H, m), 7.54 (2H, m), 8.23 (2H, m), 8.93 (2H, s)

Phase transition temperatures of the compounds of Examples 1 to 29 are shown in Table 1. The spontaneous polarization, tilt angle, and response time of these compounds are shown in Table 2 below.

TABLE 1

Phase transition temperature of 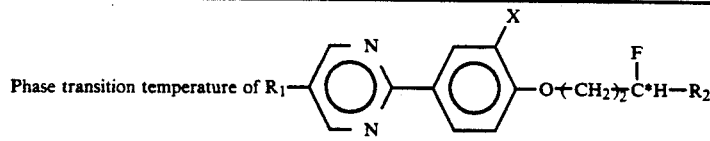

| Example No. | R₁ | R₂ | X | Steric Configuration | Cr | S₃ | Sc* | S_A | N* | I |
|---|---|---|---|---|---|---|---|---|---|---|
| 1 | C₈H₁₇ | C₄H₉ | H | R | •59.7 | | (•46.8 | | •59.7) | • |
| 2 | C₉H₁₉ | C₄H₉ | H | R | •60.7 | | (•58.7 | | •64.7) | • |
| 3 | C₉H₁₉ | C₈H₁₇ | H | R | •71.4 | | (•68.6 | | •69.5) | • |
| 4 | C₁₀H₂₁ | C₄H₉ | H | S | •68.4 | | (•62.6 | | •63.5) | • |
| 5 | C₁₂H₂₅ | C₄H₉ | H | R | •72.6 | | (•69.4) | | | • |
| 6 | C₁₂H₂₅ | C₄H₉ | H | S | •72.8 | | (•69.3) | | | • |
| 7 | C₁₂H₂₅ | CH₃ | H | R | •89.0 | | | | | • |
| 8 | C₇H₁₅O | C₅H₁₁ | H | R | •64.9 | | •75.1 | | •89.7 | • |
| 9 | C₈H₁₇O | C₃H₇ | H | R | •57.4 | | •83.7 | | •93.1 | • |
| 10 | C₈H₁₇O | C₈H₁₇ | H | R | •74.5 | | •88.5 | | •91.8 | • |
| 11 | C₁₀H₂₁O | C₄H₉ | H | S | •69.5 | | •94.2 | | | • |
| 12 | C₁₂H₂₅O | C₅H₁₁ | H | R | •74.2 | | •97.7 | | | • |
| 13 | C₈H₁₇ | C₄H₉ | F | R | •65.7 | | | | (•42.3) | • |
| 14 | C₈H₁₇ | C₅H₁₁ | F | R | •49.9 | | | | (•44.4) | • |
| 15 | C₉H₁₉ | C₄H₉ | F | R | •59.5 | | (•46.8 | | •48.5) | • |
| 16 | C₁₀H₂₁ | C₃H₇ | F | R | •52.9 | | (•40.9 | •49.1) | | • |
| 17 | C₁₀H₂₁ | C₄H₉ | F | R | •65.7 | | (•48.9 | | •49.2) | • |

TABLE 1-continued

Phase transition temperature of 
$$R_1-\underset{N}{\underset{\|}{\bigcirc}}-\underset{X}{\bigcirc}-O(CH_2)_2\overset{F}{\underset{|}{C^*H}}-R_2$$

| Example No. | $R_1$ | $R_2$ | X | Steric Configuration | Cr | $S_3$ | $Sc^*$ | $S_A$ | $N^*$ | I |
|---|---|---|---|---|---|---|---|---|---|---|
| 18 | $C_{10}H_{21}$ | $C_5H_{11}$ | F | R | •51.3 | | (•47.8 | | •51.3) | • |
| 19 | $C_{10}H_{21}$ | $C_8H_{17}$ | F | R | •50.6 | | •51.9 | | •53.4 | • |
| 20 | $C_{12}H_{25}$ | $C_3H_7$ | F | R | •64.2 | | (•45.8 | •55.6) | | • |
| 21 | $C_{12}H_{25}$ | $C_4H_9$ | F | R | •66.7 | | (•53.1 | •55.2) | | • |
| 22 | $C_{14}H_{29}$ | $C_4H_9$ | F | S | •68.9 | | (•54.6 | •58.8) | | • |
| 23 | $C_{14}H_{29}$ | $C_4H_9$ | F | R | •68.8 | | (•54.4 | •58.7) | | • |
| 24 | $C_6H_{13}O$ | $C_4H_9$ | F | S | •56.3 | | (•51.0) | •70.7 | •72.9 | • |
| 25 | $C_6H_{13}O$ | $C_8H_{17}$ | F | R | •57.3 | | (•48.0) | •67.5 | •70.8 | • |
| 26 | $C_{10}H_{21}O$ | $C_4H_9$ | F | S | •49.1 | | •81.5 | •82.0 | | • |
| 27 | 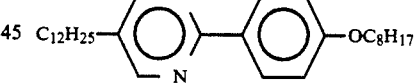 $C_{10}H_{21}$— | $C_4H_9$ | F | R | •78.2 | | •152.6 | •161.9 | | • |
| 28 | 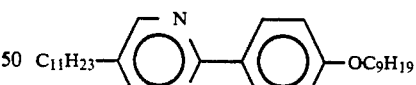 $C_{12}H_{25}$— | $C_4H_9$ | F | R | •77.8 | | •150.7 | •157.9 | | • |
| 29 | 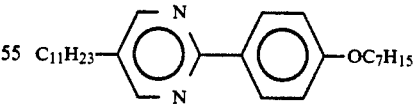 $C_9H_{17}O$— | $C_4H_9$ | F | R | •83.8 | | •176.5 | •189 | | • |

TABLE 2

| | Physical Properties (Measuring Temp. T = Tc − 5) | | |
|---|---|---|---|
| Example No. | Response Time (μsec) | Spontaneous Polarization (nC/cm²) | Tilt Angle (°C.) |
| 1 | | 55.3 | 30 |
| 2 | 13.3 | 44.2 | 25 |
| 3 | 20.9 | 42.1 | 33 |
| 4 | 10.1 | 41.6 | 24 |
| 5 | 6.8 | 36.0 | 22 |
| 6 | 7.0 | 37.6 | 22 |
| 7 | * | | |
| 8 | 16.7 | 54.9 | 32 |
| 9 | 8.9 | 37.3 | 25 |
| 10 | 12.7 | 35.7 | 28 |
| 11 | | 52.0 | 26 |
| 12 | 8.0 | 37.1 | 30 |
| 13 | * | | |
| 14 | * | | |
| 15 | 3.8 | | 7 |
| 16 | 17.7 | 21.6 | 18 |
| 17 | 10.8 | 31.4 | 17 |
| 18 | 24.2 | 28.2 | 22 |
| 19 | | 33.4 | 20 |
| 20 | 8.6 | 19.0 | 14 |
| 21 | 10.6 | 20.6 | 18 |
| 22 | 7.5 | 17.9 | 16 |
| 23 | 8.1 | 17.1 | 15 |
| 24 | ** | | |
| 25 | ** | | |
| 26 | | 36.2 | 24 |
| 27 | 3.3 | 11.2 | 22 |
| 28 | 4.8 | 9.7 | 26 |
| 29 | 2.7 | 4.2 | 15 |

Note:
*: No Sc* phase was exhibited.
**: Unmeasurable due to monotropy and rapid crystallization

EXAMPLE 30

A liquid crystal composition (A) containing the compound synthesized in Example 4 was prepared from the following components.

|  | (mol %) |
|---|---|
| 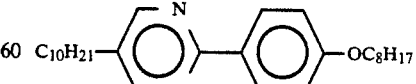 $C_{12}H_{25}$—pyridine—phenyl—$OC_8H_{17}$ | 12.5 |
| $C_{11}H_{23}$—pyridine—phenyl—$OC_9H_{19}$ | 12.6 |
| $C_{11}H_{23}$—pyridine—phenyl—$OC_7H_{15}$ | 12.5 |
| $C_{10}H_{21}$—pyridine—phenyl—$OC_8H_{17}$ | 12.7 |
| $C_{10}H_{21}$—pyridine—phenyl—$OC_6H_{13}$ | 12.5 |

-continued

| | (mol %) |
|---|---|
| C₉H₁₉—[pyrimidine]—[phenyl]—OC₇H₁₅ | 12.7 |
| S—C₁₀H₂₁—[pyrimidine]—[phenyl]—O—CH₂CH₂—C*HF—C₂H₅ | 24.5 |

Phase transition temperatures and physical properties of the liquid crystal composition (A) are shown below.

$$Cr \xrightarrow{20.2°C} Sc^* \xrightarrow{65.4°C} S_A \xrightarrow{71.1°C} I$$

| Measuring Temperature (°C.) | Ps (nC/cm²) | Tilt Angle (°) | Response Time (μsec) |
|---|---|---|---|
| 60 | 5.9 | 14.0 | 13.3 |
| 50 | 8.8 | 17.5 | 20.7 |
| 40 | 10.8 | 19.0 | 26.2 |
| 30 | 13.3 | 19.0 | 34.8 |

Phase transition temperatures of the achiral base used in the composition containing no optically active compound of the invention, were as follows.

$$Cr \xrightarrow{21.7°C} Sc \xrightarrow{63.8°C} S_A \xrightarrow{73.9°C} I$$

It can be seen that addition of the optically active compound of Example 4 does not cause a reduction in Tc and apparently broadens the temperature range for the Sc phase, thereby providing a liquid crystal composition exhibiting a fast Comparative Example 11 hereinafter given illustrates a liquid crystal composition prepared in the same manner as for composition (A) except for using the 2-fluoro compound of Comparative Example 4 in place of the compound of Example 4. This comparative composition had a faster response time than composition (A), but its Tc was lower than that of composition (A) by about 10° C. Further, the comparative composition of Comparative Example 12 using the 4-fluoro compound had a small Ps and a slow response time. Furthermore, when an ester compound was added for the purpose of broadening a temperature range as in Comparative Examples 15 and 16, the Tc was remarkably reduced with either of the 2-fluoro compound or the 4-fluoro compound being used. It is understood, therefore, that the kind of achiral liquid crystal compounds to which a 2-fluoro or 4-fluoro compound may be added as a chiral dopant is limited, and broadening of a temperature range is hardly expected with such a chiral dopant.

To the contrary, use of the 3-fluoro compound according to the present invention makes it easy to obtain a broadened temperature range including room temperature as shown in Examples 32 and 33 hereinafter described.

EXAMPLE 31

A liquid crystal composition (B) comprising the same achiral base as used in Example 30 and the compound synthesized in Example 5 as a chiral dopant was prepared from the following components.

| | (mol %) |
|---|---|
| C₁₂H₂₅—[pyrimidine]—[phenyl]—OC₈H₁₇ | 12.5 |
| C₁₁H₂₃—[pyrimidine]—[phenyl]—OC₉H₁₉ | 12.6 |
| C₁₁H₂₃—[pyrimidine]—[phenyl]—OC₇H₁₅ | 12.5 |
| C₁₀H₂₁—[pyrimidine]—[phenyl]—OC₈H₁₇ | 12.6 |
| C₁₀H₂₁—[pyrimidine]—[phenyl]—OC₆H₁₃ | 12.5 |
| C₉H₁₉—[pyrimidine]—[phenyl]—OC₇H₁₅ | 12.6 |
| S—C₁₂H₂₅—[pyrimidine]—[phenyl]—O—CH₂CH₂—C*HF—C₂H₅ | 24.7 |

Phase transition temperatures and physical properties of composition (B) are shown below.

$$Cr \xrightarrow{21.1°C} Sc^* \xrightarrow{66.9°C} S_A \xrightarrow{72.7°C} I$$

| Measuring Temperature (°C.) | Ps (nC/cm²) | Tilt Angle (°) | Response Time (μsec) |
|---|---|---|---|
| 60 | 5.9 | 14.5 | 13.8 |
| 50 | 8.7 | 18.0 | 21.0 |
| 40 | 10.4 | 19.0 | 26.2 |
| 30 | 10.9 | 19.0 | 33.0 |

Composition (B) proved to exhibit similar performances to composition (A) of Example 30.

EXAMPLE 32

A liquid crystal composition (C) containing the compound synthesized in Example 4 was prepared from the following components.

| | (mol %) |
|---|---|
| C₁₂H₂₅—[pyrimidine]—[phenyl]—OC₈H₁₇ | 11.4 |

-continued

| | (mol %) |
|---|---|
| C₁₁H₂₃—[pyridine]—[phenyl]—OC₉H₁₉ | 11.5 |
| C₁₁H₂₃—[pyridine]—[phenyl]—OC₇H₁₅ | 11.5 |
| C₁₀H₂₁—[pyridine]—[phenyl]—OC₈H₁₇ | 11.5 |
| C₁₀H₂₁—[pyridine]—[phenyl]—OC₆H₁₃ | 11.4 |
| C₉H₁₉—[pyridine]—[phenyl]—OC₇H₁₅ | 11.6 |
| (S)-C₁₀H₂₁—[pyridine]—[phenyl]—O—CH₂CH₂C*HF—C₃H₇ | 22.4 |
| C₁₂H₂₅O—[phenyl]—CO₂—[fluorophenyl]—CO₂C₈H₁₇ | 8.7 |

Phase transition temperatures and physical properties of composition (C) are shown below.

$$Cr \xrightarrow{15.0°C} Sc* \xrightarrow{50.8°C} S_A \xrightarrow{70.8°C} I$$

| Measuring Temperature (°C.) | Ps (nC/cm²) | Tilt Angle (°) | Response Time (μsec) |
|---|---|---|---|
| 40 | 4.6 | 10.0 | 6.7 |
| 30 | 6.8 | 11.0 | 12.6 |
| 20 | 8.1 | 11.0 | 16.8 |

Composition (C) contained an ester type achiral liquid crystal compound for the purpose of broadening a temperature range. As a result, the Tc dropped, but the melting point also dropped so that the temperature range of the Sc* phase was broadened including room temperature. Composition (C) exhibits a very fast response time which is similar to that of the comparative composition of Composition Example 11, the fastest of the compositions using 2-fluoro optically active compounds. Where the 2-fluoro compound was used in composition (C) in place of the compound of Example 4, the Tc was seriously reduced, failing to exhibit an Sc* phase any more.

EXAMPLE 33

A liquid crystal composition (D) containing the compound synthesized in Example 5 was prepared from the following components.

| | (mol %) |
|---|---|
| C₁₂H₂₅—[pyridine]—[phenyl]—OC₈H₁₇ | 11.5 |
| C₁₁H₂₃—[pyridine]—[phenyl]—OC₉H₁₉ | 11.6 |
| C₁₁H₂₃—[pyridine]—[phenyl]—OC₇H₁₅ | 11.6 |
| C₁₀H₂₁—[pyridine]—[phenyl]—OC₈H₁₇ | 11.6 |
| C₁₀H₂₁—[pyridine]—[phenyl]—OC₆H₁₃ | 11.5 |
| C₉H₁₉—[pyridine]—[phenyl]—OC₇H₁₅ | 11.7 |
| C₁₂H₂₅O—[phenyl]—CO₂—[fluorophenyl]—CO₂C₈H₁₇ | 8.7 |
| (R)-C₁₂H₂₅—[pyridine]—[phenyl]—O—CH₂CH₂C*HF—C₃H₇ | 21.7 |

Phase transition temperatures and physical properties of composition (D) are shown below.

$$Cr \xrightarrow{9.5°C} Sc* \xrightarrow{53.5°C} S_A \xrightarrow{70.5°C} I$$

| Measuring Temperature (°C.) | Ps (nC/cm²) | Tilt Angle (°) | Response Time (μsec) |
|---|---|---|---|
| 50 | 1.6 | 8.0 | 3.6 |
| 40 | 5.3 | 11.0 | 8.9 |
| 30 | 7.1 | 11.0 | 13.1 |
| 20 | 7.2 | 11.0 | 14.1 |

It was thus confirmed that the compound of Example 5 also provides a liquid crystal composition having a fast response time similarly to Example 32.

EXAMPLE 34

A liquid crystal composition (E) containing the compound synthesized in Example 5 was prepared from the following components.

| | (mol %) |
|---|---|
| $C_8H_{17}$—[pyrimidine]—[phenyl]—$OC_6H_{13}$ | 18.3 |
| $C_8H_{17}$—[pyrimidine]—[phenyl]—$OC_8H_{17}$ | 17.0 |
| $C_8H_{17}$—[pyrimidine]—[phenyl]—$OC_{10}H_{21}$ | 15.9 |
| $C_7H_{15}$—[pyrimidine]—[phenyl]—$OC_9H_{19}$ | 17.0 |
| $C_6H_{13}$—[pyrimidine]—[phenyl]—$OC_8H_{17}$ | 18.3 |
| (R)-$C_{12}H_{25}$—[pyrimidine]—[phenyl]—O—CH2—CHF—C3H7 | 13.7 |

Phase transition temperatures and physical properties of composition (E) are shown below.

| Measuring Temperature (°C.) | Ps (nC/cm$^2$) | Tilt Angle (°) | Response Time (μsec) |
|---|---|---|---|
| 40 | 3.0 | 12.5 | 41.6 |
| 30 | 4.8 | 17.2 | 126.2 |

Composition (E) comprises an achiral base exhibiting a nematic phase and the optically active compound of Example 5. The phase transition temperatures of the base liquid crystals are shown below.

It is seen that the compound of Example 5 easily provides a ferroelectric liquid crystal composition having a broad temperature range without reducing the Tc. On the other hand, when a 2-fluoro compound is used in place of the compound of Example 5 as in Comparative Example 13 hereinafter described, the Tc was reduced by about 10° C. to make the temperature range for the Sc* phase so much narrower. If the amount of the 2-fluoro compound to be added is decreased as in Comparative Example 14 hereinafter described, a temperature range equal to composition (E) can be assured, but substantially no improvement in response time can be obtained.

EXAMPLE 35

The optically active compound synthesized in Example 5 was added to a ferroelectric liquid crystal composition "ZLI-4237-000" produced by Merck Co. at a mixing proportion of 10.40% by weight, and any change in physical properties was examined.

Phase transition temperatures and physical properties of ZLI-4237-000 are shown below.

Cr ———— Sc* —60.5° C.— $S_A$ —69.4° C.— N* —75.2° C.— I

Physical Properties (measuring temperature: 40° C.):
Ps: 3.23 nC/cm$^2$
Tilt angle: 22.1°
Response time: 82.1 μsec (±20 V square wave applied)

Addition of the optically active compound of Example 5 brought about improvements in these physical properties without giving substantial influences on the phase transition temperatures as shown below.

Cr ———— Sc* —61.2° C.— $S_A$ —70.3° C.— N* —74.0° C.— I

Physical Properties (measuring temperature: 40° C.):
Ps 8.03 nC/cm$^2$
Tilt angle: 21.6°
Response time: 55.4 μsec (±20 V square wave applied)

It can be seen from these results that the optically active compound of the present invention, when mixed with a general ferroelectric liquid crystal composition, improves a response time without adversely affecting the temperature range.

For comparison, a liquid crystal composition was prepared in the same manner as described above, except for using a 2-fluoro compound (Comparative Example 17). Although there was no substantial difference in response time between these two compositions, the composition of Comparative Example 17 underwent reductions in Tc and angle of tilt.

In Example 35, spontaneous polarization and response time were improved without giving no substantial influences on other physical properties. Thus, the optically active compound of the present invention proved excellent as a chiral dopant.

EXAMPLE 36

The optically active compound synthesized in Example 5 and the following compound were mixed at a molar ratio of 20:80, and the rotational viscosity of the resulting composition was measured in accordance with the method described in C. Escher, et al., *Liq. Crys.*, Vol. 3, No. 4, p. 469 (1988).

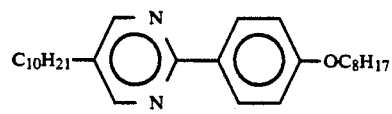

Figure 5:
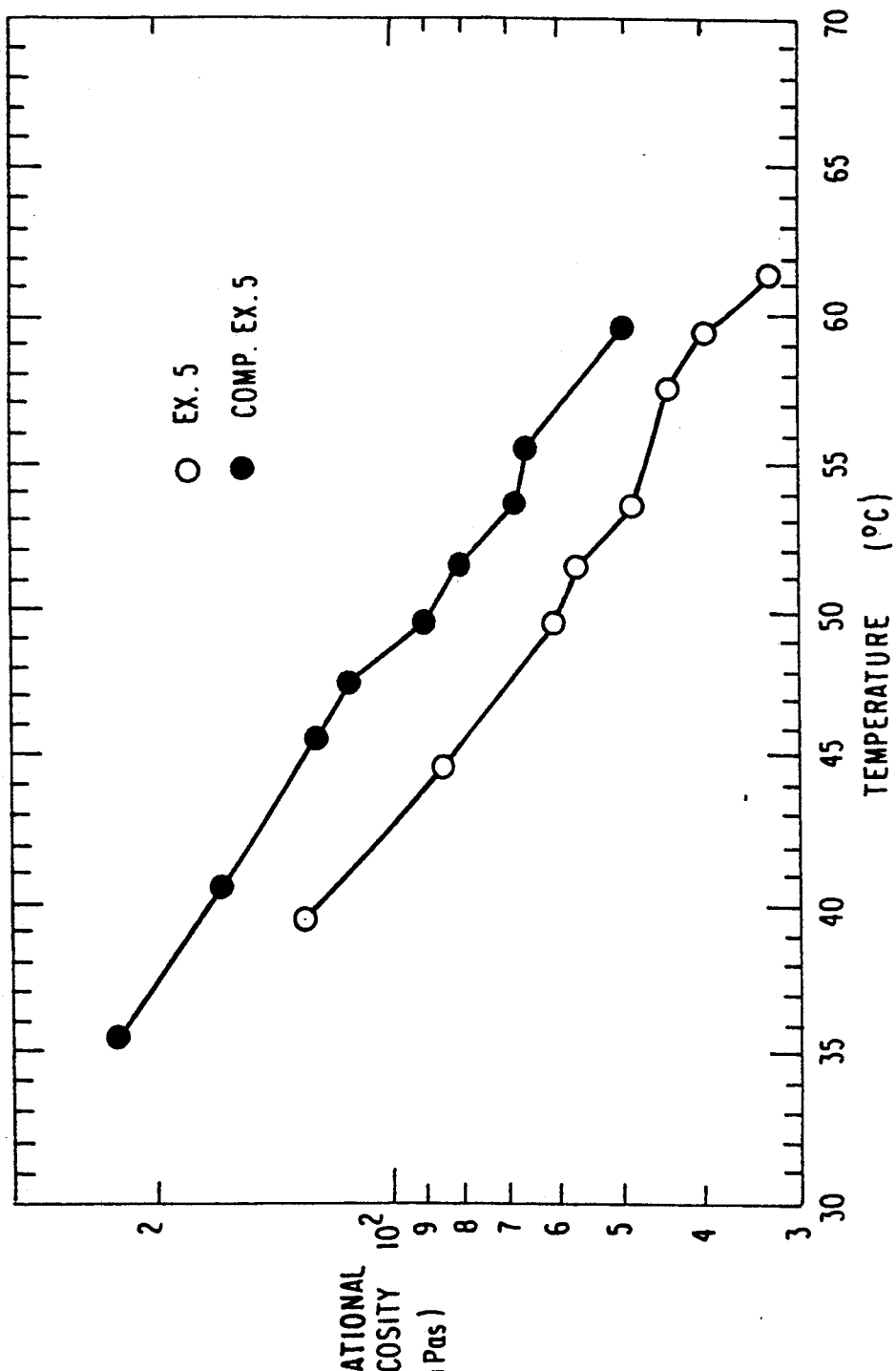
FIG. 5 is a graph showing rotational viscosity of the compositions obtained by mixing 20 mol % of the compound of Example 5 or the compound of Comparative Example 5 with 80 mol % of an achiral compound of formula.

The results obtained here and the results obtained in Comparative Example 18 are shown in FIG. 5. It can be seen that the 3-fluoro compound according to the present invention has a lower rotation viscosity than the 2-fluoro compound.

COMPARATIVE EXAMPLES 1 TO 10

Phase transition temperatures of the compounds of Comparative Examples 1 to 9; phase transition temperatures of the compound of Comparative Example 10; and physical properties of the compounds of Comparative Examples 1 to 10 are shown in Tables 3, 4, and 5, respectively.

In a 50 ml flask was charged 1.05 g of magnesium. After displacing the atmosphere with nitrogen, iodine was added thereto in a nitrogen stream to activate magnesium. Ten milliliters of dried THF was added thereto, and a solution of 6.0 g of butyl bromide in 15 ml of dried THF was added dropwise at 20° C. or lower over 1 hour. After the addition, the system was kept at that temperature for an additional period of 1.5 hours to prepare a Grignard reagent.

In a 500 ml flask were charged 150 ml of dried THF

TABLE 3

Phase transition temperature of $R_1-\underset{N}{\underset{\|}{\overset{N}{\diagdown}}}\!\!\!\!\!\!\!\!\!\!\!\!-\!\!\!\!\bigcirc\!\!\!-OCH_2-C^*H-R_2$ with F on $C^*H$

| Compara. Example No. | $R_1$ | $R_2$ | X | Steric Configuration | Cr | $S_3$ | Sc* | $S_A$ | N* | I |
|---|---|---|---|---|---|---|---|---|---|---|
| 1 | $C_{10}H_{21}$ | $C_6H_{13}$ | H | | •61 | (•49 | •62) | •71 | | • |
| 2 | $C_{10}H_{21}$ | $C_8H_{17}$ | H | | •69 | | •73 | | | • |
| 3 | $C_{12}H_{25}$ | $C_6H_{13}$ | H | | •56 | | •70 | •74 | | • |
| 4 | $C_{10}H_{21}$ | $C_5H_{11}$ | H | S | •47.5 | | •50 | •65.9 | | • |
| 5 | $C_{12}H_{25}$ | $C_5H_{11}$ | H | S | •56.3 | •57.3 | •61.3 | •70.2 | | • |
| 6 | $C_8H_{17}O$ | $C_6H_{13}$ | H | | •70 | (•48) | •80 | •96 | | • |
| 7 | $C_{11}H_{23}O$ | $C_6H_{13}$ | H | | •69 | | •99 | | | • |
| 8 | $\diagup\!\!\!\diagdown(CH_2)_9-$ | $C_6H_{13}$ | H | | •52 | | •83 | •93 | | • |
| 9 | $CF_3-(CH_2)_{11}-$ | $C_6H_{13}$ | H | | •66 | (•35) | •77 | •101 | | • |

TABLE 4

Phase transition temperature of $R_1-\underset{N}{\underset{\|}{\overset{N}{\diagdown}}}\!\!\!\!\!\!-\!\!\!\bigcirc\!(X)-O(CH_2)_3C^*H-R_2$ with F

| Compara. Example No. | $R_1$ | $R_2$ | X | Steric Configuration | Cr | $S_3$ | Sc* | $S_A$ | N* | I |
|---|---|---|---|---|---|---|---|---|---|---|
| 10 | $C_{10}H_{21}$ | $C_3H_7$ | H | R | •42.0 | | •46.8 | •66.1 | | • |

TABLE 5

| Compara. Example No. | Measuring Temperature (T − Tc) | Response Time (μsec) | Ps (nC/cm²) | Tilt Angle (°C.) |
|---|---|---|---|---|
| 1 | −4 | 10.0 | 39 | |
| 2 | −6 | 21.0 | 34 | |
| 3 | −5 | 9.9 | 36 | |
| 4 | −5 | 2.8 | 30.4 | 13 |
| 5 | −5 | 4.0 | 36.2 | 16 |
| 6 | −10 | 15.1 | 80.1 | |
| 7 | −24 | 15.2 | 105 | |
| 8 | −13 | 8.0 | 10.9 | |
| 9 | −2 | 7.1 | 14.1 | |
| 10 | −10 | 6.9 | 2.2 | 8 |

The data for Comparative Examples 1 to 3 and 6 to 9 were taken from Yahei, et al., *Dai 13-kai Ekisho Toronkai Yokoshu*, 1Z02 (1987). The compounds of Comparative Examples 4, 5, and 10 were synthesized for comparison as follows.

Synthesis of (S)-5-Dodecyl-2-[4-(2-fluoroheptyloxy)phenyl]pyrimidine (Comparative Example 5)

1) Synthesis of (R)-(−)-2-Hydroxyheptyl p-Toluenesulfonate:

and 11 ml of a 0.1M/l solution of $Li_2CuCl_4$ in THF, and the mixture was cooled to −50° C. in a nitrogen stream. The whole amount of the above prepared THF solution of $C_4H_9MgBr$ was added thereto, and the mixture was allowed to react at that temperature for 15 minutes. Then, a solution of 5.0 g of (R)-(-)-glycidyl p-toluenesulfonate in 50 ml of dried THF was added thereto over 10 minutes, followed by allowing the mixture to react at the same temperature for 1.5 hours. The resulting solution was treated with a saturated ammonium chloride aqueous solution and extracted with diethyl ether. The extract was washed with a saturated sodium chloride aqueous solution and freed of the solvent by distillation to obtain 6.4 g of a crude product. Purification of the crude product by silica gel column chromatography gave 5.3 g of the titled compound.

2) Synthesis of (R)-5-Dodecyl-2-[4-(2-hydroxyheptyloxy)phenyl]pyrimidine:

To a 100 m flask was added 0.5 g of 60% sodium hydride, and 10 ml of hexane was added thereto in a nitrogen stream. The liquid paraffin contained in the sodium hydride was removed by decantation. Then, 30 ml of dried DMF was added, and a solution of 3.0 g of 5-dodecyl-2-(4-hydroxyphenyl)pyrimidine and 3.93 g of (R)-(−)-2-hydroxyheptyl p-toluenesulfonate in 10 ml of DMF was added to the solution. The reaction mixture was allowed to react at 100° to 120° C. for 1 hour and then at 140° C. for 4 hours. The reaction mixture was poured into water and extracted with ethyl acetate. The extract was washed with a saturated sodium chloride aqueous solution and freed of the solvent by distillation to obtain 4.1 g of a crude product. The crude product was purified by silica gel column chromatography to obtain 3.1 g of the titled compound.

3) Synthesis of (S)-5-Dodecyl-2-[4-(2-fluoroheptyloxy)phenyl]pyrimidine:

In a 100 ml flask were charged 40 ml of methylene chloride and 3.1 g of (R)-5-dodecyl-2-[4-(2'-hydroxyheptyloxy)phenyl]pyrimidine, and the solution was cooled to 15° to 20° C. To the solution was added 1.98 g of hexafluoropropene diethylamine at that temperature, followed by allowing the mixture to react for 30 minutes. The reaction mixture was poured into water, neutralized with sodium hydrogencarbonate, washed with water, and freed of the solvent by distillation to obtain 4.6 g of a crude product. The crude product was purified by silica gel column chromatography and then recrystallized twice from ethanol to obtain 0.9 g of the desired compound.

MS: 428 (M+)

NMR (ppm): 0.88 (3H, m, J=6.9Hz), 0.95 (3H, t, J=7.3Hz), 1.20–1.72 (20H, m), 1.79 (2H, m), 1.97 (2H, m), 2.60 (2H, t, J=7.6Hz), 4.07 (2H, m), 4.58 (1H, m), 6.98 (3H, d, J=9.0Hz), 8.35 (2H, d, J=9.0Hz), 8.57 (2H, s)

The compound of Comparative Example 5 was mixed with ZLI-2582 in the same manner as in Example 5 (mixing ratio: 5.0 wt %), and temperature dependence of the helical pitch in the N* phase was examined. It is seen from the results shown below and FIG. 4 that the composition has considerable negative temperature dependence.

| Measuring Temp. (°C.) | N* Phase Helical Pitch (μm) |
| --- | --- |
| 30 | 29.5 |
| 40 | 19.1 |
| 50 | 14.5 |
| 60 | 12.3 |

Synthesis of
(S)-5-Decyl-2-[4-(2-fluoroheptyloxy)phenyl]pyrimidine
(Comparative Example 4)

The titled compound can be synthesized in the same manner as in Comparative Example 5 except for using 5-decyl-2-(4-hydroxyphenyl)pyrimidine in place of the 5-dodecyl-2-(4-hydroxyphenyl)pyrimidine.

Synthesis of
(R)-5-Decyl-2-[4-(4-fluoroheptyloxy)phenyl]pyrimidine (Comparative Example 10)

1) Synthesis of Methyl (S)-3-Tetrahydropyranyloxyhexanoate:

In a 500 ml flask were charged 250 ml of diethyl ether, 30 g of methyl (S)-3-hydroxyhexanoate, 20.6 g of 3,4-dihydro-2-pyran, and 0.4 g of p-toluenesulfonic acid, followed by stirring at room temperature overnight. The resulting solution was neutralized with a sodium carbonate aqueous solution and washed with water. The diethyl ether was removed by distillation under reduced pressure to obtain 48.0 g of the titled compound.

2) Synthesis of (S)-3-Tetrahydropyranyloxyhexanol:

To a 1 l flask was added 5.7 g of lithium aluminum hydride. After displacing the atmosphere with nitrogen, 400 ml of dried THF was added thereto, followed by cooling to 10° C. or lower. To the solution was added dropwise a solution of 48.0 g of methyl (S)-3-tetrahydropyranyloxyhexanoate in 200 ml of dried THF at the same temperature over 1 hour. The mixture was warmed to room temperature and stirred for 1 hour. The mixture was again cooled to 10° C. or lower, and 6 ml of water was added dropwise over 30 minutes. After the addition, 25 ml of a 4% sodium hydroxide aqueous solution was added thereto, followed by stirring at that temperature for 1 hour.

The precipitated inorganic salts were removed by filtration, and the THF layer was separated by liquid-liquid separation, dried over potassium carbonate, and freed of THF by distillation under reduced pressure to obtain 40.3 g of the titled compound.

3) Synthesis of (S)-3-Tetrahydropyranyloxyhexyl p-Toluenesulfonate:

In a 300 ml flask were charged 50 g of pyridine, 40 ml of diethyl ether, and 40.3 g of (S)-3-tetrahydropyranyloxyhexanol in a nitrogen stream, and the solution was cooled to 10° C. or less. To the solution was added tosyl chloride at that temperature over 10 minutes, followed by allowing the mixture to react at 30° C. for 2.5 hours. Water was added thereto, and the reaction mixture was extracted with diethyl ether. The extract was freed of diethyl ether by distillation under reduced pressure to obtain 71.1 g of the titled compound.

4) Synthesis of (S)-3-Tetrahydropyranyloxyhexyl Bromide:

In a 500 ml flask were charged 150 ml of dried DMF and 71.1 g of (S)-3-tetrahydropyranyloxyheptyl p-toluenesulfonate in a nitrogen stream, and 25 g of dried lithium bromide was added thereto, followed by stirring at 40° C. for 3 hours. Water was added to the reaction mixture, and the mixture was extracted with ethyl acetate. The ethyl acetate was removed from the extract by distillation under reduced pressure to obtain 42.6 g of a crude product. Purification by silica gel column chromatography yielded 19.7 g of the titled compound.

5) Synthesis of (S)-4-Tetrahydropyranyloxyheptnaol:

To a 300 ml flask was added 1.64 g of magnesium. After displacing the atmosphere with nitrogen, a small amount of iodine was added thereto, followed by warming to activate magnesium. Twenty milliliters of dried THF was added thereto, and a solution of 18 g of (S)-3-tetrahydropyranyloxyhexyl bromide in 100 ml of dried THF was added dropwise thereto using a dropping funnel over a period of 2 hours. The resulting solution was cooled to 5 to 10° C., and gaseous formaldehyde was blown thereinto for 4 hours. After stirring at that temperature for 1 hour, the reaction mixture was poured into 400 ml of an ammonium chloride aqueous solution and extracted with ethyl acetate. The ethyl acetate layer was washed with water and neutralized with sodium hydrogencarbonate. The solvent was removed by distillation under reduced pressure to obtain 12.5 g of a crude product. The crude product was purified by silica gel column chromatography to obtain 5.7 g of the titled compound.

6) Synthesis of (S)-4-Tetrahydropyranyloxyheptyl p-Toluenesulfonate:

In a 50 ml flask were charged 6.8 g of pyridine, 20 ml of diethyl ether, and 5.7 g of (S)-tetrahydropyranyloxyheptanol in a nitrogen stream, and the solution was cooled to 10° C. or lower. To the solution was added 4.6 g of tosyl chloride, followed by stirring at room temperature overnight. Water was added thereto, and the mixture was extracted with ethyl acetate. The extract was washed with water and freed of the solvent by distillation under reduced pressure to obtain 9.5 g of a crude product. Purification by silica gel column chromatography gave 4.4 g of the titled compound.

7) Synthesis of (S)-5-Decyl-2-[4-(4-tetrahydropyranyloxyheptyloxy)phenyl]pyrimidine:

In a 100 ml flask were charged 35 ml of DMF, 1.99 g of potassium carbonate, 3.0 g of 5-decyl-2-(4-hydroxyphenyl)pyrimidine, and 4.0 g of (S)-4-tetrahydropyranyloxyheptyl p-toluenesulfonate, and the mixture was allowed to react at 70° C. for 3 hours. After cooling, water was added thereto, and the reaction mixture was extracted with ethyl acetate. The extract was washed twice with water, and ethyl acetate was removed by distillation under reduced pressure to obtain 5.0 g of a crude product.

8) Synthesis of (S)-5-Decyl-2-[4-(4-hydroxyheptyloxy)phenyl]pyrimidine:

In a 50 ml flask were charged 25 ml of methanol, 5.0 g of the crude product obtained in (7) above, and 0.2 g of p-toluenesulfonic acid, and the mixture was reacted at reflux for 3 hours. Methanol was removed by distillation under reduced pressure, and the residue was extracted with ethyl acetate. The extract was neutralized with a sodium carbonate aqueous solution, washed with water, and freed of the solvent by distillation to obtain 4.0 of a crude product. Purification by silica gel column chromatography gave 2.0 of the titled compound.

9) Synthesis of (R)-5-Decyl-2-[4-(4-fluoroheptyloxy)phenyl]pyrimidine:

In a 50 ml flask were charged 2.0 g of (S)-5-n-decyl-2-[4-(4'-hydroxyheptyloxy)phenyl]pyridine and dried methylene chloride, followed by cooling to 15° C. or lower. To the solution was added 1.36 g of hexafluoropropene diethylamine over 15 minutes, followed by stirring at room temperature for 30 minutes. The reaction mixture was washed twice with water, and methylene chloride was removed therefrom by distillation under reduced pressure to obtain 1.25 g of a crude product. Purification by silica gel column chromatography and recrystallization yielded 0.67 g of the desired compound.

MS: 428 (M+)

NMR (ppm): 0.88 (3H, t, J=6.9Hz), 0.95 (3H, t, J=7.3Hz), 1.20-1.72 (20H, m), 1.79 (2H, m), 1.97 (2H, m), 2.60 (2H, t, J=7.6Hz), 4.07 (2H, m), 4.58 (1H, m), 6.98 (2H, d, J=9.0Hz), 8.35 (2H, d, J=9.0Hz), 8.57 (2H, s)

The compound of Comparative Example 10 was mixed with ZLI-2582 in the same manner as in Example 5 (mixing ratio: 5.002 wt %), and temperature dependence of the helical pitch in the N* phase was examined. It is seen from the results shown below that the composition has very small temperature dependence.

| Measuring Temp. (°C.) | N* Phase Helical Pitch (μm) |
| --- | --- |
| 30 | 21.4 |
| 40 | 21.4 |
| 50 | 21.4 |
| 60 | 21.6 |

COMPARATIVE EXAMPLE 11

A liquid crystal composition containing the optically active compound synthesized in Comparative Example 4 was prepared from the following components.

|  | (mol %) |
| --- | --- |
| $C_{12}H_{25}$—pyrimidine—$OC_8H_{17}$ | 12.5 |
| $C_{11}H_{23}$—pyrimidine—$OC_9H_{19}$ | 12.6 |
| $C_{11}H_{23}$—pyrimidine—$OC_7H_{15}$ | 12.6 |
| $C_{10}H_{21}$—pyrimidine—$OC_8H_{17}$ | 12.6 |
| $C_{10}H_{21}$—pyrimidine—$OC_6H_{13}$ | 12.5 |
| $C_9H_{19}$—pyrimidine—$OC_7H_{15}$ | 12.7 |
| (S)-$C_{10}H_{21}$—pyrimidine—O-CH-CH(F)-C_4H_9 | 24.5 |

Phase transition temperatures and physical properties of the liquid crystal composition are shown below.

$$Cr \xrightarrow{22.4°C.} Sc* \xrightarrow{56.1°C.} S_A \xrightarrow{71.1°C.} I$$

| Measuring Temperature (°C.) | Ps (nC/cm²) | Tilt Angle (°) | Response Time (μsec) |
| --- | --- | --- | --- |
| 50 | 5.8 | 12.0 | 6.1 |
| 40 | 10.5 | 13.5 | 10.1 |
| 30 | 13.6 | 13.5 | 12.0 |

COMPARATIVE EXAMPLE 12

A liquid crystal composition containing the optically active compound synthesized in Comparative Example 10 was prepared from the following components.

|  | (mol %) |
| --- | --- |
|  | 12.5 |

|  | (mol %) |
|---|---|
| C₁₁H₂₃-[pyrimidine]-[phenyl]-OC₉H₁₉ | 12.6 |
| C₁₁H₂₃-[pyrimidine]-[phenyl]-OC₇H₁₅ | 12.5 |
| C₁₀H₂₁-[pyrimidine]-[phenyl]-OC₈H₁₇ | 12.6 |
| C₁₀H₂₁-[pyrimidine]-[phenyl]-OC₆H₁₃ | 12.5 |
| C₉H₁₉-[pyrimidine]-[phenyl]-OC₇H₁₅ | 12.7 |
| (R)-C₁₀H₂₁-[pyrimidine]-[phenyl]-O-CH₂CH₂CH₂-*CH(F)-C₂H₅ | 24.5 |

Phase transition temperatures and physical properties of the liquid crystal composition are shown below.

$$Cr \xrightarrow{19.9°C} Sc* \xrightarrow{56.6°C} S_A \xrightarrow{72.1°C} I$$

| Measuring Temperature (°C) | Ps (nC/cm²) | Tilt Angle (°) | Response Time (μsec) |
|---|---|---|---|
| 50 | 0.6 | 11.5 | 54.8 |
| 40 | 1.0 | 13.0 | 71.6 |
| 30 | 1.8 | 13.0 | 100.5 |

COMPARATIVE EXAMPLE 13

A liquid crystal composition containing the optically active compound synthesized in Comparative Example 5 was prepared from the following components.

|  | (mol %) |
|---|---|
| C₈H₁₇-[pyrimidine]-[phenyl]-OC₆H₁₃ | 18.3 |
| C₈H₁₇-[pyrimidine]-[phenyl]-OC₈H₁₇ | 17.0 |
| C₈H₁₇-[pyrimidine]-[phenyl]-OC₁₀H₂₁ | 15.9 |
| C₇H₁₅-[pyrimidine]-[phenyl]-OC₉H₁₉ | 17.0 |
| C₆H₁₃-[pyrimidine]-[phenyl]-OC₈H₁₇ | 18.3 |
| (S)-C₁₂H₂₅-[pyrimidine]-[phenyl]-O-CH₂-*CH(F)-CH(CH₃)-C₄H₉ | 13.6 |

Phase transition temperatures of the liquid crystal composition are shown below.

$$Cr \xrightarrow{0.2°C} Sc* \xrightarrow{40.3°C} S_A \xrightarrow{61.9°C} N* \xrightarrow{66.1°C} I$$

COMPARATIVE EXAMPLE 14

A liquid crystal composition containing the optically active compound synthesized in Comparative Example 5 was prepared from the following components.

|  | (mol %) |
|---|---|
| C₈H₁₇-[pyrimidine]-[phenyl]-OC₈H₁₇ | 19.0 |
| C₈H₁₇-[pyrimidine]-[phenyl]-OC₁₀H₂₁ | 13.2 |
| C₇H₁₅-[pyrimidine]-[phenyl]-OC₉H₁₉ | 28.3 |
| C₇H₁₅-[pyrimidine]-[phenyl]-OC₁₁H₂₃ | 17.6 |
| C₈H₁₇-[pyrimidine]-[phenyl]-OC₁₁H₂₃ | 12.9 |
| S-C₁₂H₂₅-[pyrimidine]-[phenyl]-O-CH₂-*CH(F)-C₅H₁₁ | 9.1 |

Phase transition temperatures and physical properties of the liquid crystal composition were as follows.

Cr —6.7° C.→ Sc* —50.3° C.→ S_A —65.4° C.→ N* —68.1° C.→ I

| Measuring Temperature (°C.) | Ps (nC/cm$^2$) | Tilt Angle (°) | Response Time (μsec) |
|---|---|---|---|
| 40 | 2.9 | 16.2 | 75.0 |
| 30 | 4.3 | 20.9 | 104.4 |

COMPARATIVE EXAMPLE 15

A liquid crystal composition containing the optically active compound synthesized in Comparative Example 4 was prepared from the following components.

| | (mol %) |
|---|---|
| C$_{12}$H$_{25}$—[pyrazine]—[phenyl]—OC$_8$H$_{17}$ | 11.4 |
| C$_{11}$H$_{23}$—[pyrazine]—[phenyl]—OC$_9$H$_{19}$ | 11.5 |
| C$_{11}$H$_{23}$—[pyrazine]—[phenyl]—OC$_7$H$_{15}$ | 11.5 |
| C$_{10}$H$_{21}$—[pyrazine]—[phenyl]—OC$_8$H$_{17}$ | 11.5 |
| C$_{10}$H$_{21}$—[pyrazine]—[phenyl]—OC$_6$H$_{13}$ | 11.5 |
| C$_9$H$_{19}$—[pyrazine]—[phenyl]—OC$_7$H$_{15}$ | 11.6 |
| C$_{12}$H$_{25}$O—[phenyl]—CO$_2$—[F-phenyl]—CO$_2$C$_8$H$_{17}$ | 8.7 |
| (S)-C$_{12}$H$_{25}$—[pyrazine]—[phenyl]—O—CH$_2$—C*H(F)—C$_4$H$_9$ | 22.4 |

Phase transition temperatures of the liquid crystal composition were as follows.

Cr —15.5° C.→ S_A —71.0° C.→ I

COMPARATIVE EXAMPLE 16

A liquid crystal composition containing the optically active compound synthesized in Comparative Example 10 was prepared from the following components.

| | (mol %) |
|---|---|
| C$_{12}$H$_{25}$—[pyrazine]—[phenyl]—OC$_8$H$_{17}$ | 11.4 |
| C$_{11}$H$_{23}$—[pyrazine]—[phenyl]—OC$_9$H$_{19}$ | 11.5 |
| C$_{11}$H$_{23}$—[pyrazine]—[phenyl]—OC$_7$H$_{15}$ | 11.5 |
| C$_{10}$H$_{21}$—[pyrazine]—[phenyl]—OC$_8$H$_{17}$ | 11.5 |
| C$_{10}$H$_{21}$—[pyrazine]—[phenyl]—OC$_6$H$_{13}$ | 11.4 |
| C$_9$H$_{19}$—[pyrazine]—[phenyl]—OC$_7$H$_{15}$ | 11.6 |
| C$_{12}$H$_{25}$O—[phenyl]—CO$_2$—[F-phenyl]—CO$_2$C$_8$H$_{17}$ | 8.7 |
| R—C$_{10}$H$_{21}$—[pyrazine]—[phenyl]—O—(CH$_2$)$_4$—C*H(F)—C$_2$H$_5$ | 22.4 |

Phase transition temperatures of the liquid crystal composition were as follows.

Cr —13.8° C.→ S_A —71.8° C.→ I

COMPARATIVE EXAMPLE 17

The optically active compound synthesized in Comparative Example 5 was added to "ZLI-4237-000" at a mixing proportion of 10.05 wt %, and any change in physical properties was examined.

Phase transition temperatures and physical properties of ZLI-4237-000 are shown below.

Cr ——→ Sc* —60.5° C.→ S_A —69.4° C.→ N* —75.2° C.→ I

Physical Properties (measuring temperature: 40° C.):

Ps: 3.23 nC/cm²
Tilt angle: 22.1°
Response time: 82.1 μsec (±20 V square wave applied)

Phase transition temperatures and physical properties after the addition of the optically active compound of Comparative Example 5 were as follows.

Physical Properties (measuring temperature: 40° C.):
Ps: 7.58 nC/cm²
Tilt angle: 19.0°
Response time: 48.3 μsec (±20 V square wave applied)

It can be seen that addition of the compound of Comparative Example 5 brought about an improvement in response time, but the Tc dropped and, also, a reduction in tilt angle having an influence on contrast ratio was observed.

COMPARATIVE EXAMPLE 18

The optically active compound synthesized in Comparative Example 5 and the following compound were mixed at a molar ratio of 20:80, and the rotational viscosity of the resulting composition was measured in the same manner as in Example 36. The results are shown in FIG. 5.

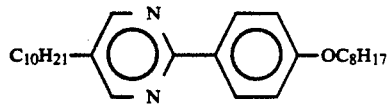

As described and demonstrated above, the optically active compounds according to the present invention, when used as a ferroelectric liquid crystal, exhibit a low viscosity and provide optoelectronic elements having a very fast response time. Further, since the compounds of the invention show a chiral nematic phase whose helical pitch has very small temperature dependence, they are useful as a chiral dopant for ferroelectric liquid crystals or nematic liquid crystals.

Moreover, a liquid crystal composition obtained by mixing the optically active compound of the present invention and a known compound showing a smectic C phase exhibits electro-optic effects with very fast switching and is useful in opto-electronic elements using liquid crystals, optical shutter arrays, and the like.

While the invention has been described in detail and with reference to specific examples thereof, it will be apparent to one skilled in the art that various changes and modifications can be made therein without departing from the spirit and scope thereof.

What is claimed is:

1. A fluorine-containing optically active compound represented by formula (I):

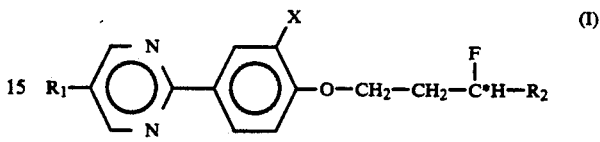

wherein $R_1$ represents a straight chain alkyl or alkoxy group having from 6 to 14 carbon atoms or a 4-alkylphenyl or 4-alkoxyphenyl group wherein the alkyl or alkoxy moiety of the 4-alkylphenyl or 4-alkoxyphenyl has from 8 to 12 carbon atoms; $R_2$ represents a straight chain alkyl group having from 1 to 8 carbon atoms; C* represents an asymmetric carbon atom; and X represents a hydrogen atom or a fluorine atom, provided that X represents a fluorine atom when $R_1$ contains a phenyl group and when X is a hydrogen atom, $R_1$ is not a straight chain alkyl group.

2. A liquid crystal composition containing a fluorine-containing optically active compound represented by formula (I):

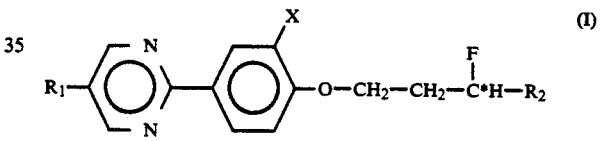

wherein $R_1$ represents a straight chain alkyl or alkoxy group having from 6 to 14 carbon atoms or a 4-alkylphenyl or 4-alkoxyphenyl group wherein the alkyl or alkoxy moiety of the 4-alkylphenyl or 4-alkoxyphenyl has from 8 to 12 carbon atoms; $R_2$ represents a straight chain alkyl group having from 1 to 8 carbon groups; C* represents an asymmetric carbon atom; and X represents a hydrogen atom or a fluorine atom, provided that X represents a fluorine atom when $R_1$ contains a phenyl group and when X is a hydrogen atom, $R_1$ is not a straight chain alkyl group.

* * * * *